United States Patent
Choi et al.

(10) Patent No.: US 9,951,150 B2
(45) Date of Patent: Apr. 24, 2018

(54) AMINOSILANE TERMINAL MODIFIER TO WHICH FUNCTIONAL GROUP HAS BEEN INTRODUCED, METHOD FOR PRODUCING TERMINAL-MODIFIED CONJUGATED DIENE POLYMER USING THE AMINOSILANE TERMINAL MODIFIER, AND TERMINAL-MODIFIED CONJUGATED DIENE POLYMER PRODUCED ACCORDING TO THE METHOD

(71) Applicant: LG Chem, Ltd., Seoul (KR)

(72) Inventors: Seung-Ho Choi, Daejeon (KR);
Min-Soo Kim, Daejeon (KR);
Cheol-Jae Kim, Daejeon (KR);
Won-Mun Choi, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 15/125,809

(22) PCT Filed: Oct. 22, 2015

(86) PCT No.: PCT/KR2015/011233
§ 371 (c)(1),
(2) Date: Sep. 13, 2016

(87) PCT Pub. No.: WO2016/104931
PCT Pub. Date: Jun. 30, 2016

(65) Prior Publication Data
US 2017/0002104 A1 Jan. 5, 2017

(30) Foreign Application Priority Data

Dec. 22, 2014 (KR) .......... 10-2014-0186008
Jul. 23, 2015 (KR) .......... 10-2015-0104528

(51) Int. Cl.
| | |
|---|---|
| *C08L 15/00* | (2006.01) |
| *C08C 19/25* | (2006.01) |
| *C08F 36/06* | (2006.01) |
| *C08C 19/22* | (2006.01) |
| *C08C 19/44* | (2006.01) |
| *C08F 236/10* | (2006.01) |
| *C08K 3/36* | (2006.01) |
| *C08K 5/544* | (2006.01) |
| *C08C 19/26* | (2006.01) |
| *C07F 7/18* | (2006.01) |
| *C08F 236/06* | (2006.01) |

(52) U.S. Cl.
CPC ............. *C08C 19/25* (2013.01); *C07F 7/184* (2013.01); *C07F 7/1836* (2013.01); *C08C 19/22* (2013.01); *C08C 19/26* (2013.01); *C08C 19/44* (2013.01); *C08F 36/06* (2013.01); *C08F 236/06* (2013.01); *C08F 236/10* (2013.01); *C08K 3/36* (2013.01); *C08K 5/544* (2013.01); *C08L 15/00* (2013.01); *C08F 2500/03* (2013.01); *C08F 2810/40* (2013.01)

(58) Field of Classification Search
None
See application file for complete search history.

(56) References Cited

U.S. PATENT DOCUMENTS

| | | | |
|---|---|---|---|
| 3,033,815 A | 5/1962 | Pike et al. | |
| 3,746,738 A | 7/1973 | Pepe et al. | |
| 4,067,844 A * | 1/1978 | Barron ................ | C08G 18/10 |
| | | | 524/588 |
| 5,128,416 A | 7/1992 | Imai et al. | |
| 7,858,690 B2 * | 12/2010 | Chen .................. | C08C 19/44 |
| | | | 524/492 |
| 8,378,094 B2 * | 2/2013 | Shooshtari ........ | C03C 25/18 |
| | | | 540/487 |
| 2005/0159554 A1 | 7/2005 | Endou et al. | |
| 2014/0018500 A1 | 1/2014 | Luo | |
| 2015/0376321 A1 | 12/2015 | Lee et al. | |

FOREIGN PATENT DOCUMENTS

| | | |
|---|---|---|
| DE | 1114326 B | 9/1961 |
| DE | 1171235 B | 5/1964 |
| EP | 0341496 A2 | 11/1989 |
| EP | 2826793 A1 | 1/2015 |
| JP | 2004018587 A | 1/2004 |
| JP | 2008208376 A | 9/2008 |
| JP | 2013060525 A | 4/2013 |
| JP | 2013082842 A | 5/2013 |
| JP | 2013119558 A | 6/2013 |
| JP | 2013245248 A | 12/2013 |
| JP | 2014177519 A | 9/2014 |
| JP | 2015196684 A | 11/2015 |
| KR | 20060012403 A | 2/2006 |

(Continued)

OTHER PUBLICATIONS

Hideharu Mori "Design and Synthesis of Functional Silsesquioxane-Based Hybrids by Hydrolytic Condensation of Bulky Triethoxysilanes" International Journal of Polymer Science, 2012, 1-17.*
Mori et al. "Film-Forming amphiphilic silsesquioxane hybrids prepared by hydrolytic co-condensation of hydroxyl-functionalized and fluorinated triethoxysilanes" Polymer, 53, 2012, 3849-3860.*
Mori, et al., "Synthesis and characterization of low-refractive-index fluorinated silsesquioxane-based hybrids." Polymer, vol. 52, 2011, pp. 5452-5463.
Extended European Search Report for Application No. 15873459.0, dated Apr. 5, 2017.
International Search Report for Application No. PCT/KR2015/011229 dated Feb. 2, 2016.

(Continued)

*Primary Examiner* — Robert S Loewe
(74) *Attorney, Agent, or Firm* — Lerner, David, Littenberg, Krumholz & Mentlik, LLP

(57) ABSTRACT

Disclosed are an end-modified conjugated diene-based polymer configured such that the end of a conjugated diene-based polymer is coupled with an aminosilane-based end modifier, and a method of preparing the same.

10 Claims, No Drawings

(56) References Cited

FOREIGN PATENT DOCUMENTS

| KR | 20060126908 A | 12/2006 |
|----|---------------|---------|
| KR | 20130090811 A | 8/2013 |
| KR | 101461416 B1 | 11/2014 |
| KR | 20140127726 A | 11/2014 |
| WO | 2014175561 A1 | 10/2014 |

OTHER PUBLICATIONS

International Search Report from PCT/KR2015/011233, dated Feb. 11, 2016.
Extended Search Report from European Application No. 15873458.2, dated Oct. 28, 2016.
Database WPI Week 200707, Thomson Scientific, London, GB; AN 2007-065950, XP002763145.
Chaussee, Thomas, "Elastomer Compositions Modified by Silanes." IP.com Journal, IP.com Inc., West Henrietta, NY US, Dec. 15, 2011, XP013148631.

* cited by examiner

AMINOSILANE TERMINAL MODIFIER TO WHICH FUNCTIONAL GROUP HAS BEEN INTRODUCED, METHOD FOR PRODUCING TERMINAL-MODIFIED CONJUGATED DIENE POLYMER USING THE AMINOSILANE TERMINAL MODIFIER, AND TERMINAL-MODIFIED CONJUGATED DIENE POLYMER PRODUCED ACCORDING TO THE METHOD

CROSS-REFERENCE TO RELATED APPLICATION

This application is a national phase entry under 35 U.S.C. § 371 of International Application No. PCT/KR2015/011233, filed Oct. 22, 2015, which claims priority to Korean Patent Application No. 10-2014-0186008, filed Dec. 22, 2014 and Korean Patent Application No. 10-2015-0104528, filed Jul. 23, 2015, the disclosures of which are incorporated herein by reference.

TECHNICAL FIELD

The present invention relates to a functionalized aminosilane-based end modifier, a method of preparing an end-modified conjugated diene-based polymer using the same, and an end-modified conjugated diene-based polymer prepared thereby.

BACKGROUND ART

Recently, in the vehicle industry, the demand for the durability, stability and fuel economy of vehicles is continuously increasing, and much effort is directed to satisfying the demand.

In particular, many attempts have been made to enhance the properties of rubber, as a material for vehicle tires, especially tire treads, which are in contact with roads. The rubber composition for a vehicle tire contains a conjugated diene-based polymer, such as polybutadiene or butadiene-styrene copolymer.

Thorough research is currently ongoing into the addition of various reinforcing agents to conjugated diene-based rubber compositions to increase the performance of vehicle tires. Specifically, as vehicles are required to exhibit stability, durability and fuel economy, rubber compositions having high processability and mechanical strength, including wear resistance, are being developed as material for vehicle tires, especially tire treads, which are in contact with roads.

DISCLOSURE

Technical Problem

An object of the present invention is to provide an end modifier for a conjugated diene-based polymer to increase the processability and mechanical strength, including wear resistance, of the conjugated diene-based polymer, which is contained in a rubber composition.

Another object of the present invention is to provide a method of preparing an end-modified conjugated diene-based polymer using the end modifier.

Still another object of the present invention is to provide an end-modified conjugated diene-based polymer prepared by the method.

Technical Solution

In order to accomplish the above objects, an aspect of the present invention provides an end-modified conjugated diene-based polymer configured such that the end of a conjugated diene-based polymer is coupled with an aminosilane-based end modifier represented by Chemical Formula 1 below:

[Chemical Formula 1]

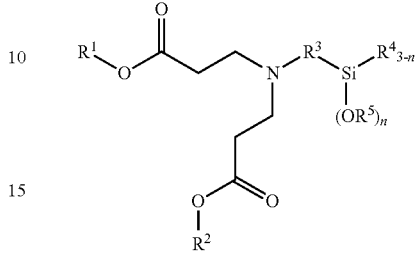

in Chemical Formula 1, $R^1$ and $R^2$ are a C1-C20 hydrocarbon, or a C1-C20 hydrocarbon containing a heteroatom, $R^3$ is a C1-C10 hydrocarbon, $R^4$ and $R^5$ are a C1-C20 hydrocarbon, and n is an integer of 1 to 3.

In addition, another aspect of the present invention provides a method of preparing an end-modified conjugated diene-based polymer, comprising: a) polymerizing a conjugated diene monomer or a conjugated diene monomer and an aromatic vinyl monomer using a hydrocarbon solvent in the presence of an organometallic compound, thus forming an active polymer having an alkali metal end; and b) modifying the active polymer having the alkali metal end with a compound represented by Chemical Formula 1 below:

[Chemical Formula 1]

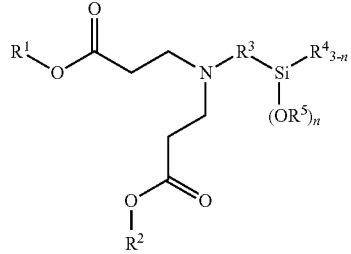

in Chemical Formula 1, $R^1$ and $R^2$ are a C1-C20 hydrocarbon, or a C1-C20 hydrocarbon containing a heteroatom, $R^3$ is a C1-C10 hydrocarbon, $R^4$ and $R^5$ are a C1-C20 hydrocarbon, and n is an integer of 1 to 3.

In addition, still another aspect of the present invention provides an aminosilane-based end modifier represented by Chemical Formula 1 below:

[Chemical Formula 1]

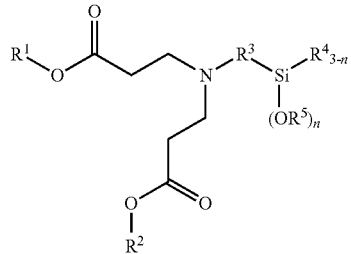

in Chemical Formula 1, $R^1$ and $R^2$ are a C1-C20 hydrocarbon, or a C1-C20 hydrocarbon containing a heteroatom, $R^3$ is a C1-C10 hydrocarbon, $R^4$ and $R^5$ are a C1-C20 hydrocarbon, and n is an integer of 1 to 3.

Advantageous Effects

According to the present invention, an end-modified conjugated diene-based polymer includes an aminosilane end modifier that is substituted with a group including not only a tertiary amine group, but also a silica-compatible group or a hexane-compatible group. The tertiary amine group can prevent aggregation due to hydrogen bonding between hydroxyl groups on the surface of the silica, thus increasing the dispersion of the silica, and the silica-compatible group can increase wear resistance and processability by virtue of interactions with the silica. Furthermore, the hexane-compatible group is effective at increasing modification efficiency by increasing solubility in hexane.

Also, in the aminosilane-based modifier according to the present invention, when the number of alkoxy groups that react with silica is increased to achieve high molecular weight and high modification efficiency, Mooney viscosity is increased through hydrolysis and condensation. In order to solve the problem whereby viscosity increases during storage of the polymer, two carbonyl groups having high reactivity are introduced to the anionic end, thereby preventing Mooney viscosity from increasing due to hydrolysis and condensation and further increasing the end anion reactivity to thus enable selective reaction with the carbonyl groups.

Best Mode

Hereinafter, a detailed description will be given of the present invention.

An aspect of the present invention addresses an end-modified conjugated diene-based polymer configured such that the end of a conjugated diene-based polymer is coupled with the aminosilane-based end modifier represented by Chemical Formula 1 below:

[Chemical Formula 1]

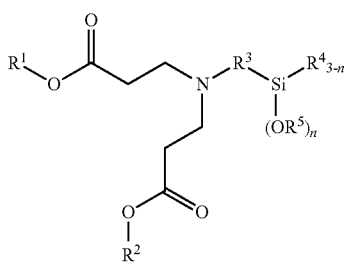

in Chemical Formula 1, $R^1$ and $R^2$ are a C1-C20 hydrocarbon, or a C1-C20 hydrocarbon containing a heteroatom, $R^3$ is a C1-C10 hydrocarbon, $R^4$ and $R^5$ are a C1-C20 hydrocarbon, and n is an integer of 1 to 3.

In Chemical Formula 1, the heteroatom may be N, S or O.

In Chemical Formula 1, $R^1$ and $R^2$ may be a C1-C10 alkyl group, or a C1-C10 alkyl group containing a heteroatom.

In Chemical Formula 1, $R^3$ may be a C1-C10 alkylene group.

In Chemical Formula 1, $R^4$ and $R^5$ may be a C1-C20 alkyl group.

The end-modified conjugated diene-based polymer has a number average molecular weight (Mn) of 1,000 to 2,000,000 g/mol, preferably 10,000 to 2,000,000 g/mol, and more preferably 100,000 to 2,000,000 g/mol.

The end-modified conjugated diene-based polymer has a molecular weight distribution (Mw/Mn) of 1.05 to 10, preferably 1.1 to 5, and more preferably 1.1 to 4. When the molecular weight distribution of the end-modified conjugated diene-based polymer falls in the above range, the resulting rubber composition may be imparted with improved mechanical properties, fuel economy and wear resistance.

The end-modified conjugated diene-based polymer has a vinyl content of 5 wt % or more, preferably 10 wt % or more, and more preferably 15 to 70 wt %.

The vinyl content refers to the amount of a monomer having a vinyl group, or the amount not of 1,4-added conjugated diene monomer but of 1,2-added conjugated diene monomer, based on 100 wt % of the conjugated diene monomer.

When the vinyl content of the end-modified conjugated diene-based polymer falls in the above range, the glass transition temperature of the polymer may be elevated. Thus, when such a polymer is applied to tires, the properties required of tires, such as running resistance and braking force, may be satisfied, and superior fuel economy may result.

The end-modified conjugated diene-based polymer may include a conjugated diene-based polymer chain, corresponding to a polymer chain comprising the aromatic vinyl monomer in an amount of 1 to 60 wt %, 10 to 50 wt %, or 15 to 40 wt %, based on 100 wt % in total of the conjugated diene monomer and the aromatic vinyl monomer.

The polymer chain may be, for example, a random polymer chain.

The conjugated diene monomer may include at least one selected from the group consisting of 1,3-butadiene, 2,3-dimethyl-1,3-butadiene, piperylene, 3-butyl-1,3-octadiene, isoprene, and 2-phenyl-1,3-butadiene.

The aromatic vinyl monomer may include at least one selected from the group consisting of styrene, α-methylstyrene, 3-methylstyrene, 4-methylstyrene, 4-propylstyrene, 1-vinylnaphthalene, 4-cyclohexylstyrene, 4-(p-methylphenyl)styrene, and 1-vinyl-5-hexylnaphthalene. Preferably useful is styrene or α-methylstyrene.

Another aspect of the present invention addresses a method of preparing an end-modified conjugated diene-based polymer, comprising: a) polymerizing a conjugated diene monomer or a conjugated diene monomer and an aromatic vinyl monomer using a hydrocarbon solvent in the presence of an organometallic compound, thus forming an active polymer having an alkali metal end; and b) modifying the active polymer having the alkali metal end with a compound represented by Chemical Formula 1 below:

[Chemical Formula 1]

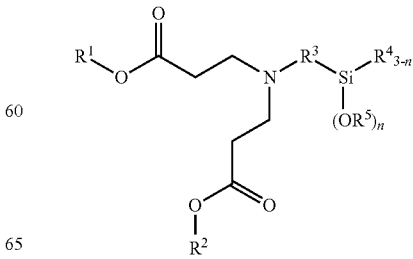

in Chemical Formula 1, $R^1$ and $R^2$ are a C1-C20 hydrocarbon, or a C1-C20 hydrocarbon containing a heteroatom, $R^3$ is a C1-C10 hydrocarbon, $R^4$ and $R^5$ are a C1-C20 hydrocarbon, and n is an integer of 1 to 3.

The conjugated diene monomer and the aromatic vinyl monomer are as described above.

The solvent is not particularly limited, so long as it may be applied in the polymerization or copolymerization of the conjugated diene monomer, and may be exemplified by a hydrocarbon, or may include at least one selected from the group consisting of n-pentane, n-hexane, n-heptane, isooctane, cyclohexane, toluene, benzene, and xylene.

The organometallic compound may be exemplified by an organo-alkali metal compound, or may include at least one selected from the group consisting of an organolithium compound, an organosodium compound, an organopotassium compound, an organorubidium compound, and an organocesium compound.

For example, the organometallic compound may include at least one selected from the group consisting of methyllithium, ethyllithium, isopropyllithium, n-butyllithium, sec-butyllithium, tert-butyllithium, n-decyllithium, tert-octyllithium, phenyllithium, 1-naphthyllithium, n-eicosyllithium, 4-butylphenyllithium, 4-tolyllithium, cyclohexyllithium, 3,5-di-n-heptylcyclohexyllithium, and 4-cyclopentyllithium. Preferably, the organometallic compound is n-butyllithium, sec-butyllithium or a mixture thereof.

Alternatively, the organometallic compound may include at least one selected from the group consisting of naphthyl sodium, naphthyl potassium, lithium alkoxide, sodium alkoxide, potassium alkoxide, lithium sulfonate, sodium sulfonate, potassium sulfonate, lithium amide, sodium amide, and potassium amide, and may be used in combination with another organometallic compound.

In an embodiment of the present invention, the organometallic compound may be used in an amount of 0.01 to 10 mmol, 0.05 to 5 mmol, 0.1 to 2 mmol, or 0.1 to 1 mmol, based on 100 g in total of the monomer. When the amount of the organometallic compound falls in the above range, a conjugated diene-based polymer optimal for use in the preparation of an end-modified conjugated diene-based polymer may be obtained.

The molar ratio of the organometallic compound and the compound represented by Chemical Formula 1 may range from 1:0.1 to 1:10, and preferably 1:0.3 to 1:2. When the molar ratio thereof falls in the above range, the conjugated diene-based polymer may be subjected to a modification reaction to ensure optimal performance.

As used herein, the active polymer having the metal end refers to a polymer comprising a polymer anion and a metal cation, which are coupled with each other.

In the method of preparing the end-modified conjugated diene-based polymer according to an embodiment of the present invention, the polymerizing in a) may be performed with the additional use of a polar additive. The reason why the polar additive is further added is that the reaction rates of the conjugated diene monomer and the aromatic vinyl monomer are controlled by the polar additive.

The polar additive may be a base, or may include ether, amine or mixtures thereof. Specifically, it may be selected from the group consisting of tetrahydrofuran, ditetrahydrofurylpropane, diethylether, cyclopamylether, dipropylether, ethylenedimethylether, ethylenedimethylether, diethyleneglycol, dimethylether, tert-butoxyethoxyethane bis(2-dimethylaminoethyl)ether, (dimethylaminoethyl)ethylether, trimethylamine, triethylamine, tripropylamine, and tetramethylethylenediamine. Preferably useful is ditetrahydropropylpropane, triethylamine, or tetramethylethylenediamine.

The polar additive may be used in an amount of 0.001 to 50 g, 0.001 to 10 g, 0.005 to 1 g, or 0.005 to 0.1 g, based on 100 g in total of the added monomer.

The polar additive may be used in an amount of 0.001 to 10 g, 0.005 to 1 g, or 0.005 to 0.1 g, based on 1 mmol in total of the added organometallic compound.

When the conjugated diene monomer and the aromatic vinyl monomer are copolymerized, a block copolymer may be readily prepared due to the difference in the reaction rates therebetween. However, when the polar additive is added, the low reaction rate of the aromatic vinyl monomer may be increased to thus obtain the microstructure of the corresponding copolymer, for example, a random polymer.

In a), the polymerization may be exemplified by anionic polymerization. Specifically, the polymerization in a) may be living anionic polymerization in which an active end is obtained through a growth reaction involving anions.

Also, the polymerization in a) may be either high-temperature polymerization or room-temperature polymerization.

High-temperature polymerization is a polymerization process that comprises adding the organometallic compound and then applying heat to increase the reaction temperature, and room-temperature polymerization is a polymerization process that takes place in such a way that heat is not applied after the organometallic compound is added.

The polymerization in a) may take place at a temperature ranging from −20 to 200° C., 0 to 150° C., or 10 to 120° C.

In b), at least one, or two or three, selected from among compounds represented by Chemical Formula 1, may be added.

Also, b) may be carried out at 0 to 90° C. for 1 min to 5 hr.

The method of preparing the end-modified conjugated diene-based polymer according to an embodiment of the present invention may be carried out in a batch manner, or alternatively in a continuous manner using at least one reactor.

Still another aspect of the present invention addresses an aminosilane-based end modifier represented by Chemical Formula 1 below:

[Chemical Formula 1]

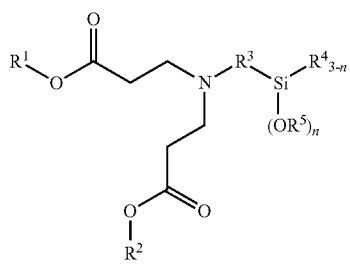

in Chemical Formula 1, $R^1$ and $R^2$ are a C1-C20 hydrocarbon, or a C1-C20 hydrocarbon containing a heteroatom, $R^3$ is a C1-C10 hydrocarbon, $R^4$ and $R^5$ are a C1-C20 hydrocarbon, and n is an integer of 1 to 3.

In Chemical Formula 1, the heteroatom may be N, S or O.

In Chemical Formula 1, $R^1$ and $R^2$ may be a C1-C10 alkyl group, or a C1-C10 alkyl group containing a heteroatom.

In Chemical Formula 1, $R^3$ may be a C1-C10 alkylene group.

In Chemical Formula 1, $R^4$ and $R^5$ may be a C1-C20 alkyl group.

The end modifier according to the present invention is an aminosilane-based end modifier, in which an aminosilane derivative is substituted with a group including not only a tertiary amine group, but also a silica-compatible group such as an ethyleneglycol group or a hexane-compatible group such as an alkyl group or aryl group. In the end modifier, the tertiary amine group may increase the dispersion of silica and function as a catalyst for the reaction, and the silica-compatible group may play a role in increasing the wear resistance and processability of the polymer by reacting with silica. Also, the modifier including a hexane-compatible group may increase the solubility of the polymer in hexane, ultimately increasing the modification efficiency of the polymer.

Preferably, Chemical Formula 1 is represented by Chemical Formula 1a below.

[Chemical Formula 1a]

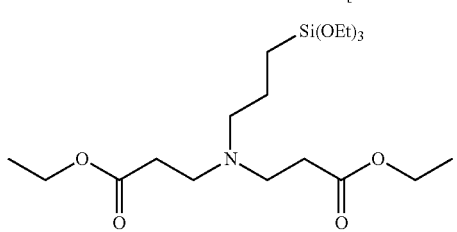

Mode for Invention

A better understanding of the present invention may be obtained via the following examples, which are merely set forth to illustrate the present invention, and those skilled in the art will appreciate that various changes and modifications are possible, without departing from the scope and spirit of the invention as disclosed in the accompanying claims.

Preparation Example 1

Preparation of diethyl 3,3'-((3-(triethoxysilyl)propyl)azanediyl)dipropionate 23.26 mmol of (3-aminopropyl)triethoxysilane was dissolved in 10 mL of ethanol in a 50 mL round-bottom flask, 46.53 mmol of ethyl acrylate was added, and the resulting mixture was stirred at 80° C. for 24 hr in a nitrogen atmosphere. After termination of the reaction, the solvent was removed under reduced pressure, followed by vacuum distillation at 80° C., yielding 22.36 mmol (yield 96.1%) of diethyl 3,3'-((3-(triethoxysilyl)propyl)azanediyl)dipropionate. The $^1$H NMR data of the purified diethyl 3,3'-((3-(triethoxysilyl)propyl)azanediyl)dipropionate is as follows:

$^1$H-NMR (500 MHz, CDCl$_3$) δ 4.07-4.03 (m, 4H), δ 3.77-3.72 (m, 6H), δ 2.72-2.69 (t, 4H), δ 2.37-2.34 (t, 6H), δ 1.49-1.43 (m, 2H), δ 1.20-1.14 (m, 15H), δ 0.52-0.49 (t, 2H).

Preparation of End-Modified Styrene-Butadiene Polymer

Example 1

270 g of styrene, 710 g of 1,3-butadiene, 5 kg of n-hexane, and 1.1 g of DTP (2,2-di(2-tetrahydrofuryl)propane) as a polar additive were placed in a 20 L autoclave reactor, and the temperature inside the reactor was elevated to 40° C. When the temperature inside the reactor reached 40° C., 27 g (2.62 wt % in hexane, 33% activation) of n-butyllithium was added to the reactor, followed by an adiabatic heating reaction. After about 30 min, 20 g of 1,3-butadiene was added so that the end of SSBR was capped with butadiene. After 5 min, the modifier of Preparation Example 1, that is, 1.64 g of diethyl 3,3'-((3-(triethoxysilyl)propyl)azanediyl) dipropionate was added, and the reaction was carried out for 15 min. Thereafter, the polymerization was stopped using ethanol, and 33 g of a solution of a Wingstay K antioxidant dissolved at 30 wt % in hexane was added. The resulting polymer was added to water warmed with steam, stirred to remove the solvent, and then roll-dried to remove the remaining solvent and water, yielding an end-modified conjugated diene-based polymer. The sample was dried and measured via GPC.

The results of analysis of the end-modified conjugated diene-based polymer thus obtained are shown in Table 1 below.

Comparative Example 1

An end-modified conjugated diene-based polymer was prepared in the same manner as in Example 1, with the exception that N,N-bis(triethoxysilylpropyl)piperazine was used as the end modifier.

TABLE 1

| | GPC (× 10$^4$) | | | | |
| --- | --- | --- | --- | --- | --- |
| | Mn | Mw | Mp | Coupling efficiency (%) | Molecular weight distribution (Mw/Mn) |
| Ex. 1 | 41 | 64 | Mp1 23 | 38 | 1.5 |
| | | | Mp2 68 | 62 | |
| C.Ex. 1 | 34 | 45 | Mp1 25 | 43 | 1.3 |
| | | | Mp2 53 | 57 | |

When the polymerization was performed using the end modifier of Example 1 according to the present invention, the coupling efficiency was increased. The number of triethoxysilanes was less than the number of N,N-bis(triethoxysilylpropyl)piperazines of Comparative Example 1, but the coupling efficiency of the polymer component was increased (62%), the reason for which is considered to be that the number of ester groups having high reactivity was increased by 1 in the end anion of rubber.

The invention claimed is:

1. An end-modified conjugated diene-based polymer configured such that an end of a conjugated diene-based polymer is coupled with an aminosilane-based end modifier represented by Chemical Formula 1 below:

[Chemical Formula 1]

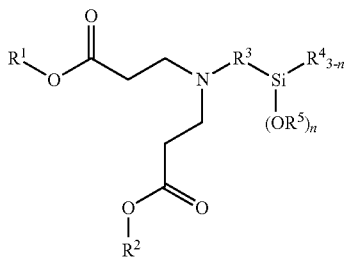

in Chemical Formula 1, $R^1$ and $R^2$ are a C1-C20 hydrocarbon, or a C1-C20 hydrocarbon containing a heteroatom, $R^3$ is a C1-C10 hydrocarbon, $R^4$ and $R^5$ are a C1-C20 hydrocarbon, and n is an integer of 1 to 3.

2. The end-modified conjugated diene-based polymer of claim 1, wherein the Chemical Formula 1 is represented by Chemical Formula 1a below:

[Chemical Formula 1a]

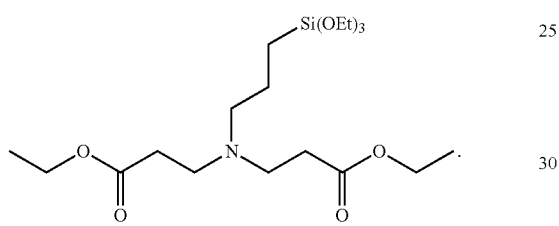

3. The end-modified conjugated diene-based polymer of claim 1, wherein the end-modified conjugated diene-based polymer has a number average molecular weight (Mn) of 1,000 to 2,000,000 g/mol.

4. The end-modified conjugated diene-based polymer of claim 1, wherein the end-modified conjugated diene-based polymer comprises 1 to 60 wt % of an aromatic vinyl monomer based on 100 wt % in total of a conjugated diene monomer and the aromatic vinyl monomer.

5. A method of preparing an end-modified conjugated diene-based polymer, comprising:
 a) polymerizing a conjugated diene monomer or a conjugated diene monomer and an aromatic vinyl monomer using a hydrocarbon solvent in presence of an organometallic compound, thus forming an active polymer having an alkali metal end; and
 b) modifying the active polymer having the alkali metal end with a compound represented by Chemical Formula 1 below:

[Chemical Formula 1]

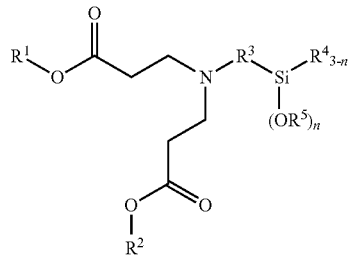

in Chemical Formula 1, $R^1$ and $R^2$ are a C1-C20 hydrocarbon, or a C1-C20 hydrocarbon containing a heteroatom, $R^3$ is a C1-C10 hydrocarbon, $R^4$ and $R^5$ are a C1-C20 hydrocarbon, and n is an integer of 1 to 3.

6. The method of claim 5, wherein the Chemical Formula 1 is represented by Chemical Formula 1a below:

[Chemical Formula 1a]

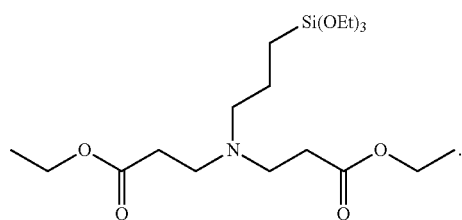

7. The method of claim 5, wherein the organometallic compound is used in an amount of 0.01 to 10 mmol based on 100 g in total of the monomer.

8. The method of claim 5, wherein a molar ratio of the organometallic compound and the compound represented by Chemical Formula 1 ranges from 1:0.1 to 1:10.

9. The method of claim 5, wherein the polymerizing in a) is performed with additional use of a polar additive.

10. The method of claim 9, wherein the polar additive is added in an amount of 0.001 to 10 g based on 1 mmol in total of the organometallic compound.

* * * * *